United States Patent [19]

Kinney

[11] 4,450,090
[45] May 22, 1984

[54] THICKENED ALPHA-OLEFIN SULFONATE CONTAINING FORMULATIONS

[75] Inventor: James Kinney, Ramsey, N.J.

[73] Assignee: Clairol Incorporated, New York, N.Y.

[21] Appl. No.: 494,756

[22] Filed: May 16, 1983

[51] Int. Cl.³ .................. C11D 1/14; C11D 3/48
[52] U.S. Cl. .................. 252/106; 252/174.18; 252/174.21; 252/315.3; 252/546; 252/548; 252/555; 252/DIG. 13; 252/DIG. 14; 536/4.1; 536/116
[58] Field of Search .......... 252/106, 174.17, 174.18, 252/174.21, 536, 555, 545, 546, 548, 315.3, DIG. 13, DIG. 14; 536/4.1, 116, 119

[56] References Cited

U.S. PATENT DOCUMENTS

| | | | |
|---|---|---|---|
| 3,435,024 | 3/1969 | Nobile et al. | 536/4.1 |
| 3,785,985 | 1/1974 | Grand | 252/106 |
| 4,177,171 | 12/1979 | Walts | 252/541 |
| 4,196,201 | 4/1980 | Boelle et al. | 424/180 |
| 4,261,851 | 4/1981 | Duke | 252/174.21 |
| 4,329,334 | 5/1982 | Su et al. | 424/70 |
| 4,367,169 | 1/1983 | Matsushita et al. | 252/542 |

FOREIGN PATENT DOCUMENTS 68352 1/1983 European Pat. Off.
2011462 7/1979 United Kingdom.

*Primary Examiner*—P. E. Willis, Jr.
*Attorney, Agent, or Firm*—Gabriel P. Katona

[57] ABSTRACT

A di($C_{12}$–$C_{22}$ unsaturated higher fatty acid) ester of a polyethoxylated glucoside of the formula

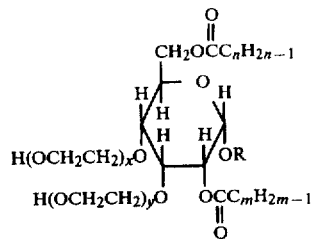

wherein
R is a hydrogen atom or ($C_1$–$C_4$) alkyl,
n is a number of from 12 to 22,
m is a number of from 12 to 22, and
x and y are positive numbers such that $110 \leq x+y \leq 150$.

was found to be an excellent thickener for alpha-olefin sulfonate surfactants.

14 Claims, No Drawings

THICKENED ALPHA-OLEFIN SULFONATE CONTAINING FORMULATIONS

BACKGROUND OF THE INVENTION

1. Field of the Invention

This invention relates to thickening agents for alpha-olefin sulfonate surfactants and particularly to alpha-olefin sulfonate shampoo and liquid soap formulations which are thickened with a novel thickening agent.

2. Discussion of the Prior Art

Cleaning compositions, such as soaps and shampoos, containing alpha-olefin sulfonate surfactants have become increasingly popular in recent years in view of their low cost relative to alcohol sulfates, such as sodium lauryl sulfate which is generally considered to be the dominant surfactant in liquid cleaning compositions. The popularity of the alpha-olefin sulfonates (AOS) has been made possible by the development of the continuous falling film process using continuous thin-film reactors employing gaseous $SO_3$, such as described, for example, in U.S. Pat. No. 3,142,169 to Knaggs and Nussbaum. However, because of their different chemical properties and formulating properties from the alcohol sulfates, for example, their viscosity response characteristics and foaming characteristics, the use of AOS surfactants has not been as widespread as possible.

It is generally known that the formulating characteristics of AOS surfactants can be modified to more closely correspond to that of the alcohol sulfate salts, such as sodium lauryl sulfate, by control of such variables as pH, salt level and type of salt, selection of foam boosting aids, and the like. The use of $C_{10}$–$C_{15}$ primary alkanols for producing rich, stable, creamy wet lathers from AOS formulations is taught in U.S. Pat. No. 3,870,660 to Paviak. Nevertheless, the problem still remains in that none of the known thickening agents or thickened AOS formulations are capable of providing stable compositions with sufficiently high viscosities. Still further, the foaming characteristics of conventional alpha-olefin sulfonate formulations have not been entirely satisfactory.

Accordingly, it is an object of the present invention to provide alpha-olefin sulfonate containing formulations with viscosities as high as or higher than alcohol sulfate salts or other surface-active agents.

It is another object of the present invention to provide thickened shampoo and liquid soap formulations based on alpha-olefin sulfonate surface-active agents having viscosities of at least 200 cps and which produce thick and stable foams.

It is still a further object of the present invention to provide alpha-olefin sulfonate shampoo formulations of improved stability, foam richness, texture and wet combing properties.

It is still a further object of the present invention to provide a thickening agent for alpha-olefin sulfonate containing shampoos, liquid soaps and other cleaning formulations to provide a rich, thick, stable lather type foam.

SUMMARY OF THE INVENTION

These and other objects of the present invention have been accomplished based on applicants' discovery that di($C_{12}$–$C_{22}$ unsaturated higher fatty acid) esters of polyethoxylated glucoside of the formula

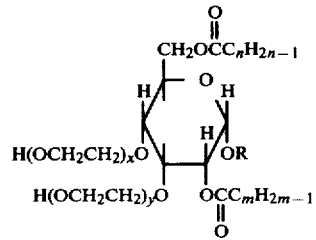

wherein
R is a hydrogen atom or ($C_1$–$C_4$)alkyl,
n is a number of from 12 to 22,
m is a number of from 12 to 22, and
x and y are positive numbers such that $110 \leq x+y \leq 150$ is a unique thickening agent for alpha-olefin sulfonate surfactants. Accordingly, the present invention provides thickened foamable aqueous compositions containing an alpha-olefin sulfonate surfactant and a di($C_{12}$–$C_{22}$ unsaturated higher fatty acid) ester of polyethoxylated glucoside having the above formula.

In a preferred embodiment of the invention, the thickening properties of the ethoxylated glucoside are synergistically enhanced by further incorporating into the composition at least one amide or betaine foam booster selected from higher fatty alkanolamides and higher fatty amidoalkylbetaines.

The present invention also provides a method for increasing the viscosity of alpha-olefin sulfonate containing formulations by adding to the formulation an effective amount of the polyethoxylated glucoside thickening agent of the above formula.

DETAILED DESCRIPTION OF THE INVENTION AND PREFERRED EMBODIMENTS

Surface-active compounds typically contain two distinct portions in their molecules: a hydrophobic oleophilic portion which is typically a straight or branched chain hydrocarbon; and a hydrophilic portion which may be charged or uncharged. When formulated in a typical liquid composition such as a shampoo, the surface-active molecules will solubilize throughout the solution and align themselves in greater concentration at all interfaces (solution/air; solution/glass container; solution/dispersed cosmetic ingredients). It is this property which makes them surface-active.

In their alignment, surface-active materials tend to arrange themselves so that the hydrophilic water-loving portion of the molecule will orient towards the aqueous phase while the hydrophobic portion orients towards non-polar substrates, such as air, glass, oil dispersions, etc. This alignment at the interface of solution and air reduces the force which is necessary to penetrate that interface, i.e. a noted reduction in surface tension (dynes/cm$^2$) is observed. When the interfacial area experiences mechanical motion as in the shampooing of hair, the interface becomes stretched. During this stretching, the concentration of surfactant per unit of area at the solution/air interface decreases as the surfactant molecules become spread further apart.

As a consequence of this surface stretching, several physico-chemical phenomena can occur:

(1) The solution can instantaneously release additional surfactant molecules to fill in the gaps, in which case there is little interfacial change and proportionally little foaming (low elasticity);

(2) Other components of the formula can interfere with the release of the solution's surfactant to the interface. Temporarily, this will result in a localized build-up of cohesive solution forces (elasticity) and surface tension. This increase in cohesive forces will allow the solution to be stretched without bursting so that foaming (bubble formation) can occur.

The raw materials most commonly used in the cosmetic industry to interfere with surfactant replacement during interfacial film-stretching are the alkanolamides (secondary surfactants). Unlike the primary anionic shampoo surfactant which is typically sodium lauryl sulfate, the hydrophilic portions of the secondary surfactant are nonionic. This allows close proximity to the anionic hydrophilic portion of the primary surfactant. On the hydrophobic end, the lauryl portion of the anionic detergent (primary surfactant) is chemically similar to the saturated fatty acid portion of the alkanolamide. Here again, this chemical similarity improves solubility of the alkanolamide and allows close proximity to the primary anionic detergent.

However, an entirely different situation exists with the alpha-olefin sulfonates, which represent a unique, unsaturated anionic detergent. The present inventors have discovered that the unsaturated portion of the alpha-olefin sulfonate surface-active agents requires an unsaturated additive to maximize solubility and interference with sulfonate replacement during the interfacial film stretching. This observation has lead to the discovery that enhanced thickening, i.e. stabilized foam and viscosity control, of the alpha-olefin sulfonates is provided by the class of surface-active agents which are higher unsaturated fatty acid diesters of glucosides which are ethoxylated with at least about 110 ethoxy groups. Thus, as can be seen from the following Table I an unsaturated secondary surfactant will produce greater viscosities in alpha-olefin sulfonate formulations than a similar saturated molecule while still further highly substantial thickening effects are obtained with the ethoxylated glucoside unsaturated higher fatty acid diesters.

TABLE I

| Viscosity of Secondary Surfactants in 14% A.O.S./Water Shampoo | |
|---|---|
| 10% Secondary Surfactant in 14% A.O.S./Water | Viscosity (TB, 3 rpm, 3 min 25° C.) cps |
| Stearoyl Sarcosine ($C_{18}$ Saturated) | 3,000 |
| Oleoyl Sarcosine ($C_{18}$ Unsaturated) | 59,000 |
| Glucamate DOE-120* (Ethoxylated Glucoside-$C_{18}$—Oleic Side Chains) | 109,725 |

*A product of Amerchol Inc.

The discovery that the above glucoside dioleate molecule will thicken alpha-olefin sulfonate (A.O.S.) containing shampoo and liquid soap formulations and similar cleaning compositions and the degree of the thickening activity was completely unexpected in view of the thickening activity in A.O.S./water solutions of state of the art thickeners as shown in the following Table II and in view of the thickening activity of the glucoside dioleate in typical shampoo and liquid soap detergents as compared to the thickening activity in A.O.S. solutions as shown in the following Table III.

TABLE II

Glucoside Dioleate Thickening Activity In
10.8% Alpha Olefin Sulfonate (A.O.S.) Water Solutions
vs. State Of The Art Thickeners

| | | Viscosity-cps Of A.O.S. Solutions Containing | |
|---|---|---|---|
| Thickening Agent Added to A.O.S./ Water Solns. | | 5% Thickener | 10% Thickener |
| a. | Lauric/Myristic DEA | 5* | 1400 |
| b. | Coco Amido Alkyl Betaine | 3* | 200 |
| c. | Ethoxylated (120) Methyl Glucoside Dioleate | 220* | 40,000 |
| d. | 2½% (a) + 2½% (c) | 8.0 | — |
|    | 5% (a) + 5% (c) | — | 23,400* |
| e. | 2½% (b) + 2½% (c) | 1 | — |
|    | 5% (b) + 5% (c) | — | 20,400* |

TABLE III

Comparison Of Glucoside Dioleate Thickening
Activities In Typical Shampoo/Liquid Soap
Detergents vs. Alpha Olefin Sulfonate
(A.O.S.)

| | Viscosity cps. Wt. % Glucoside Dioleate Added | | |
|---|---|---|---|
| 27% Active Detergent/ Water Solns. | 0% | 5% | 10% |
| Sodium Lauryl Sulfate | 10 | 10 | 30,750 |
| Sodium Lauryl Ether Sulfate | 10 | 80 | 73,815 |
| Ammonium Lauryl Sulfate | 10 | 10 | 13,250 |
| Alpha Olefin Sulfonate | 10 | 205 | 93,100 |

Furthermore, from the above Table II, the synergistic (*) thickening action between the ethoxylated glucoside diester and conventional state of the art alkanolamide or betaine thickeners (foam boosters or secondary surfactants) is apparent.

Alpha-olefin sulfonates are reaction products formed by sulfonating an alpha-olefin which has been synthesized by either oligomerization of ethylene or via thermo-cracking of paraffin wax. Alpha-olefin sulonates generally are comprised of a major proportion of sodium 2,3-alkenylsulfonate and a minor proportion of sodium 3-hydroxy-alkanesulfonate of the formula R—CH=CH—CH$_2$—SO$_3$Na and

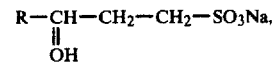

respectively, wherein R is a linear or branched alkyl of from about 8 to about 20 carbon atoms. Typically in most commercially available A.O.S. surfactants, R is a blend of $C_{14-16}$ or $C_{16-18}$ chain length and accordingly, the $C_{14-16}$ and $C_{16-18}$ alpha-olefin sulfonates are preferred for use in the thickened A.O.S. compositions of the present invention.

Polyoxyethylenated mono- and di-aliphatic carboxylates of alpha-methyl glucoside corresponding to the following formula:

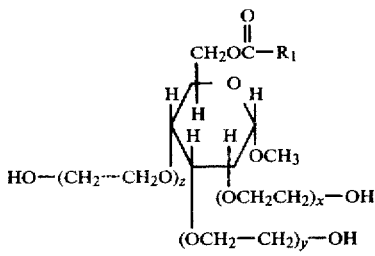

in which

R₁ represents a linear or branched saturated or unsaturated aliphatic radical having from 11 to 21 carbon atoms, and $x+y(+z)$ generally represent from 10 to 30 inclusive, are broadly disclosed in British Patent Specification GB No. 2,011,462A, published July 11, 1979, as a surface-active agent for use in a non-irritant cosmetic composition for the removal of eye makeup. However, the only specific surface-active agent actually disclosed in this patent application is the Amerchol product sold under the tradename "Glucamate SSE-20" which is a mixture of the mono- and di-stearate of alpha-methylglucoside oxyethylenated with 20 moles of ethylene oxide.

In contrast, the ethoxylated glucoside derivatives of the present invention which are useful as thickening agents for A.O.S. formulations are the unsaturated higher fatty acid diesters of glucoside or alpha-lower alkyl glucoside which are ethoxylated with at least 110 moles of ethylene oxide. Accordingly, the thickening agents of the present invention are the ethoxylated glucosides of the following formula:

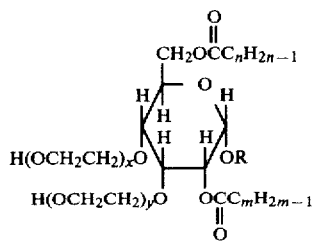

wherein

R is a hydrogen atom or $(C_1-C_4)$alkyl, especially $C_1-C_2$ alkyl, and especially preferably methyl, n is a number of from 12 to 22, preferably from 14 to 20, and especially preferably about 17 on the average, m is a number of from 12 to 22, preferably 14 to 20, and especially preferably 17 on the average, and x and y are positive numbers such that $110 \leq x+y \leq 150$, especially the sum of $x+y$ is about 120 to 140, especially preferably about 120.

Particularly good results have been obtained with the product Glucamate DOE-120, available from Amerchol, Inc. as a thickening agent for sodium lauryl ether sulfate. Glucamate DOE-120 has the formula

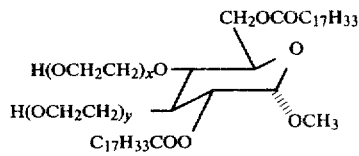

in which $x+y=120$. Glucamate DOE-120 can be prepared by reacting 1 mole methyl glucoside with 2 moles oleic acid ($C_{17}H_{33}COOH$) in the presence of a suitable esterification catalyst to form the corresponding dioleate ester. The dioleate ester is then ethoxylated with ethylene oxide. These reaction steps are, per se, well known in the art, and can be readily adapted to the other glucoside diesters within the scope of the invention.

It should also be appreciated that while preferred thickening agents for the alpha-olefin sulfonate detergents are the ethoxylated glucoside diesters as described above, the corresponding monoesters can also be used for their thickening activity in place of some or all of the diesters. However, in view of the fact that the diesters are more readily commercially available and are easier to prepare, the diesters are particularly especially preferred.

The amount of the alpha-olefin surfactant and ethoxylated glucoside higher fatty acid diester will depend on the end use of the formulation and the desired viscosity and foamability. Generally, however, amounts of the alpha-olefin sulfonate of at least about 2% by weight of the solution, preferably at least about 4% by weight, for example, about 4% to about 40%, preferably from about 4% to about 30% by weight based on the total weight of the composition of the alpha-olefin sulfonate is satisfactory for most shampoo and liquid soap formulations. The amount of the higher fatty acid ester of the polyethoxylated glucoside need only be that amount sufficient to provide the desired viscosity for the thickened foamable aqueous composition, generally, viscosities of at least 200 cps, especially at least about 500 cps and up to about 150,000 cps, especially up to about 100,000 cps or higher. Generally, amounts of the ethoxylated glucoside diester in the range of from about 1% to about 20% by weight of the composition, preferably from about 5% to 20% by weight and especially preferably from about 8% to about 15% by weight of the composition provide satisfactory viscosity and foaming characteristics.

As mentioned above, it has also been discovered that the thickening action of the polyethoxylated glucoside diesters can be synergistically enhanced by the incorporation in the formulations of at least one secondary surfactant (foam booster) of the alkanolamide or betaine class. Preferred foam boosters include the higher fatty acid ($C_8-C_{18}$) alcohol amides such as lauric diethanolamide, myristic diethanolamide, coco diethanolamide, oleo diethanolamide and the like, and these may be used singly or in mixtures. Examples of the alkyl betaine foam boosters include, for example, the higher fatty acid amido($C_1-C_4$)alkyl betaines such as exemplified by cocoamidopropylbetaine, as well as the higher fatty acid betaines such as oleyl betaine. Mixtures of the alkanolamide and betaine additives can also be used.

The total amount of the secondary surfactant (foam booster) is generally in the amount of from about 0.1 to 20% by weight, preferably from about 1 to 15% by weight of the total composition.

In addition to the above mentioned components, any of the conventional cosmetic liquid or solid additives can be included within the compositions of the present invention. These can include, for example, preservatives, coloring agents, perfumes, solubilizing agents, alcohols, fillers, builders, polymers, bactericides and germicides, as well as specific additives such as antidandruff agents such as zinc compounds, cadmium sulfide and the like.

In addition to the enchanced thickening and foaming characteristics imparted to alpha-olefin sulfonate containing formulations, it has additionally been discovered in side-by-side comparisons that the polyethoxylated glucoside diesters substantially enhance the wet combing characteristics of hair care products such as shampoos and hair conditioning compositions.

Typical examples of the thickened alpha-olefin sulfonate formulations which can be improved by the thickening agents of the present invention are shown below:

Clear Shampoo

| Ingredient | Broad Range wt % | Preferred Range wt % |
|---|---|---|
| (a) Alpha olefin sulfonate surfactant, e.g. $C_{14}$-$C_{16}$ or $C_{16}$-$C_{18}$ alpha-olefin sulfonates | 2–40 | 3–30 |
| (b) $C_{12}$-$C_{22}$ unsaturated fatty acid diester of a glucoside polyethoxylated with from 110 to 150 mole of ($OCH_2CH_2$), e.g. ethoxylated (120) methyl glucoside dioleate | 1–20 | 5–20 |
| (c) At least one $C_8$-$C_{18}$ fatty acid alkanolamide foam boosting agent, e.g. lauric/myristic diethanolamide | 0–10 | 0.1–8 |
| (d) At least one $C_8$-$C_{18}$ fatty acid amide ($C_1$-$C_4$) alkyl betaine foam boosting agent, e.g. coco amido alkyl betaine | 0–10 | 0.1–8 |
| (e) Quaternary Ammonium Salt e.g. Quaternium-60, Quaternium-8 to Quaternium-71 | 0–3 | 0.1–2 |
| (f) Preservative, e.g. methyl paraben, propyl paraben, etc. | 0–0.5 | 0–0.5 |
| (g) Color | 0–0.1 | 0–0.1 |
| (h) Water | q.s. to 100% | q.s. to 100% |

Viscosity Range 500–100,000+ cps.

Liquid Soap

| Ingredient | Broad Range wt % | Preferred Range wt % |
|---|---|---|
| (a) Alpha olefin sulfonate surfactant, e.g. $C_{14}$-$C_{16}$ or $C_{16}$-$C_{18}$ alpha-olefin sulfonates | 2–40 | 3–30 |
| (b) $C_{12}$-$C_{22}$ unsaturated fatty acid diester of a glucoside polyethoxylated with from 110 to 150 mole of ($OCH_2CH_2$), e.g. ethoxylated (120) methyl glucoside dioleate | 1–20 | 5–20 |
| (c) At least one $C_8$-$C_{18}$ fatty acid alkanolamide foam boosting agent, e.g. lauric/myristic diethanolamide | 0–10 | 0.1–8 |
| (d) At least one $C_8$-$C_{18}$ fatty acid amide ($C_1$-$C_4$) alkyl betaine foam boosting agent, e.g. oleyl betaine | 0–10 | 0.1–8 |
| (e) Solubilizing agent, e.g. propylene glycol | 1–5 | 1–5 |
| (f) Preservative, e.g. methyl paraben | 0.05–0.5 | 0.05–0.5 |
| (g) Perfume | 0–1 | 0–1 |
| (h) Color | 0–0.1 | 0–0.1 |
| (i) Water | q.s. to 100% | q.s. to 100% |

Viscosity Range 500–100,000+ cps.

Antidandruff Shampoo

| Ingredient | Broad Range wt % | Preferred Range wt % |
|---|---|---|
| (a) Alpha olefin sulfonate surfactant, e.g. $C_{14}$-$C_{16}$ or $C_{16}$-$C_{18}$ alpha-olefin sulfonates | 2–40 | 3–30 |
| (b) $C_{12}$-$C_{22}$ unsaturated fatty acid diester of a glucoside polyethoxylated with from 110 to 150 mole of ($OCH_2CH_2$), e.g. ethoxylated (120) methyl glucoside dioleate | 1–20 | 5–20 |
| (c) At least one $C_8$-$C_{18}$ fatty acid alkanolamide foam boosting agent, e.g. lauric/myristic diethanolamide | 0.1–10 | 0.5–8 |
| (d) Magnesium Aluminum Silicate | 0.1–3 | 0.3–2 |
| (e) Zinc Compound antidandruff agent, e.g. zinc-2-pyridine-thiol-1-oxide, zinc pyrithione, zinc pyridinethione, etc. | 0.1–3 | 0.5–2.0 |
| | 0.5–2.0 | 0.5–2.0 |
| (f) Perfume | 0–1 | 0–1 |
| (g) Color | 0–0.1 | 0–0.1 |
| (h) Water | q.s. to 100% | q.s. to 100% |

Viscosity Range 500–100,000+ cps.

What we claim is:

1. A thickened foamable aqueous composition comprising an alpha-olefin sulfonate surfactant and a di($C_{12}$-$C_{22}$ unsaturated higher fatty acid) ester of a polyethoxylated glucoside of the formula

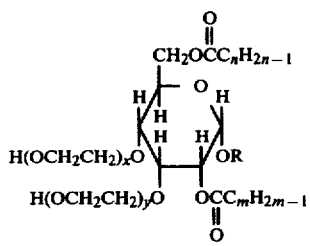

wherein
R is a hydrogen atom or ($C_1$-$C_4$) alkyl,
n is a number of from 12 to 22,
m is a number of from 12 to 22, and
x and y are positive numbers such that $110 \leq x+y \leq 150$.

2. The composition of claim 1 wherein $x+y$ is about 120 to 140.

3. The composition of claim 1 wherein R is methyl.

4. The composition of claim 1 wherein n and m are each about 17 on the average.

5. The composition of claim 1 which further comprises at least one of a higher fatty alkanolamide and a higher fatty amidoalkyl betaine.

6. The composition of claim 1 wherein the amount of the alpha olefin sulfonate surfactant is in the range of from about 2% to about 40% and the amount of the polyethoxylated glucoside thickening agent is in the range of from about 1% to about 20%, each based on the total weight of the composition.

7. The composition of claim 6 which further comprises from about 0.1% to about 20%, based on the total composition, of at least one secondary surfactant foam boosting agent selected from the group consisting of higher fatty acid alkanolamides and higher fatty acid amidoalkyl betaines.

8. A method for increasing viscosity of a liquid alpha-olefin sulfonate surfactant formulation which comprises adding to the formulation an effective amount of a compound of the formula:

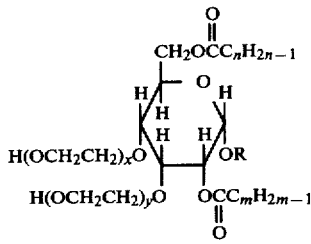

wherein
R is a hydrogen atom or ($C_1$–$C_4$) alkyl,
n is a number of from 12 to 22,
m is a number of from 12 to 22, and
x and y are positive numbers such that $110 \leq x+y \leq 150$.

9. An aqueous hair shampoo composition comprising:

| Ingredient | Amount (weight %) |
|---|---|
| (a) Alpha-olefin sulfonate surfactant | 2–40 |
| (b) $C_{12}$–$C_{22}$ unsaturated fatty acid diester of a glucoside polyethoxylated with from 110 to 150 moles of ($OCH_2CH_2$) | 1–20 |
| (c) At least one $C_8$–$C_{18}$ fatty acid alkanolamide foam boosting agent | 0–10 |
| (d) At least one $C_8$–$C_{18}$ fatty acid amido ($C_1$–$C_4$)alkyl betaine foam boosting agent | 0–10 |
| (e) Quaternary Ammonium Salt | 0–3 |
| (f) Preservative | 0–0.5 |
| (g) Coloring agent | 0–0.1 |
| (h) Water | q.s. to 100%. |

10. The shampoo composition of claim 9 which comprises:

| | |
|---|---|
| 3–30% | (a) |
| 5–20% | (b) |
| 0.1–8% | (c) |
| 0.1–8% | (d) |
| 0.1–2% | (e) |
| .0–0.1% | (f) |
| 0–0.1% | (g) | and the balance water.

11. A liquid soap composition comprising

| Ingredient | Amount (Weight %) |
|---|---|
| (a) Alpha-olefin sulfonate surfactant | 2–40 |
| (b) $C_{12}$–$C_{22}$ unsaturated fatty acid diester of a glucoside polyethoxylated with from 110 to 150 moles of ($OCH_2CH_2$) | 1–20 |
| (c) At least one $C_8$–$C_{18}$ fatty acid alkanolamide foam boosting aid | 0–10 |
| (d) At least one $C_8$–$C_{18}$ alkyl betaine foam boosting aid | 0–10 |
| (e) Propylene glycol solubilizing agent | 1–5 |
| (f) Preservative | 0.05–0.5 |
| (g) Perfume | 0–1 |
| (h) Color | 0–0.1 |
| (i) Water | q.s. to 100%. |

12. The liquid soap composition of claim 11 which comprises:

| | |
|---|---|
| 3–30% | (a) |
| 5–20% | (b) |
| 0.1–8% | (c) |
| 0.1–8% | (d) |
| 1–5% | (e) |
| 0.05–0.5% | (f) |
| 0–1% | (g) |
| 0–0.1% | (h) | and balance water.

13. An antidandruff shampoo composition comprising:

| Ingredient | Amount (Weight %) |
|---|---|
| (a) Alpha-olefin sulfonate surfactant | 2–40 |
| (b) $C_{12}$–$C_{22}$ unsaturated fatty acid diester of a glucoside polyethoxylated with from 110 to 150 moles of ($OCH_2CH_2$) | 1–20 |
| (c) At least one $C_8$–$C_{18}$ fatty acid alkanolamide foam boosting agent | 0.1–10 |
| (d) Magnesium aluminum silicate | 0.1–3 |
| (e) Zinc compound antidandruff agent | 0.1–3 |
| (f) Perfume | 0–1 |
| (g) Color | 0–0.1 |
| (i) Water | q.s. to 100%. |

14. The antidandruff shampoo of claim 13 which comprises:

| | |
|---|---|
| 3–30% | (a) |
| 5–20% | (b) |
| 0.5–8% | (c) |
| 0.3–2% | (d) |
| 0.5–2.0% | (e) |
| 0–1% | (f) |
| 0–0.1% | (g) | and the balance water, said zinc compound (e) being at least one of zinc-2-pyridinethiol-1-oxide, zinc pyrithione or zinc pyridinethione.

* * * * *